United States Patent [19]

Thomas et al.

[11] Patent Number: 5,411,024
[45] Date of Patent: May 2, 1995

[54] FETAL PULSE OXIMETRY SENSOR

[75] Inventors: Simon W. H. Thomas, New Haven; William R. Pruehsner, Meriden, both of Conn.

[73] Assignee: Corometrics Medical Systems, Inc., Wallingford, Conn.

[21] Appl. No.: 167,334

[22] Filed: Dec. 15, 1993

[51] Int. Cl.⁶ .............................................. A61B 5/00
[52] U.S. Cl. ................................... 128/634; 128/633; 128/664; 128/665
[58] Field of Search ............................... 128/633–634, 128/639, 642, 664–665; 356/39–41

[56] References Cited

U.S. PATENT DOCUMENTS

| Re. 28,990 | 10/1976 | Hon et al. | |
|---|---|---|---|
| 3,827,428 | 8/1974 | Hon et al. | |
| 4,281,645 | 8/1981 | Jobsis | 128/633 |
| 4,510,938 | 4/1985 | Jobsis et al. | 128/633 |
| 4,644,957 | 2/1987 | Ricciardelli et al. | 128/642 |
| 4,658,825 | 4/1987 | Hochberg et al. | 128/634 |
| 4,913,151 | 4/1990 | Harui et al. | 128/634 |
| 4,938,218 | 7/1990 | Goodman et al. | 128/633 |
| 5,109,849 | 5/1992 | Goodman et al. | 128/633 |
| 5,152,299 | 10/1992 | Soukup | |
| 5,154,175 | 10/1992 | Gunther | 128/633 |
| 5,247,932 | 9/1993 | Chung et al. | 128/633 |

FOREIGN PATENT DOCUMENTS

| 2677547 | 12/1992 | France | 128/642 |
|---|---|---|---|
| 09016 | 10/1989 | WIPO | . |
| 9118549 | 12/1991 | WIPO | 128/634 |

Primary Examiner—Angela D. Sykes
Attorney, Agent, or Firm—Michael, Best & Friedrich

[57] ABSTRACT

A fetal pulse oximetry sensor device containing a pulse oximetry sensor is disclosed. The device also includes a spiral for fetal attachment. One or both of the light emitting portion and light detecting portion of the pulse oximetry sensor is spring biased to be moveable with respect to the body of the device. Alternatively, the light emitting portion and light detecting portion may be mounted within the housing of the device, with the housing being spring biased towards the fetal skin. In this manner, the pulse oximetry sensor is maintained in intimate contact with the fetal tissue. This provides for accurate oximetry measurements since the errors due to the detection of unattenuated or non-absorbed light passing directly from the light emitter to the light detector, are significantly reduced. The fetal attachment spiral may also include a fetal EKG electrode, in which case the device may be used as both a fetal pulse oximeter and a fetal heart rate monitor.

23 Claims, 4 Drawing Sheets

FETAL PULSE OXIMETRY SENSOR

FIELD OF THE INVENTION

The invention relates to a device for use in monitoring the functional oxygen saturation of a fetus.

BACKGROUND OF THE INVENTION

U.S. Pat. No. Re 28,990, which is incorporated herein by reference, discloses a bipolar fetal electrode assembly commonly used to monitor fetal heart rate during birth. When using such an assembly, a physician inserts the forward end of a curved guide tube through the mother's vagina and cervix until the forward end of the guide tube makes contact with the fetal head or other portion of the fetus. Holding the forward end of the guide tube stationary, the physician then pushes the rear end of a flexible driving tube forwardly until a spiral fetal electrode at the forward end of one wire of a twisted pair of wires makes contact with the fetal epidermis. The forward end of the other wire has a spade-like reference electrode which is electrically isolated from the spiral fetal electrode.

The physician then rotates the flexible driving tube clockwise about one full turn while maintaining the forward end of the guide tube against the fetal head. This causes the spiral electrode to screw into the fetal epidermis. Thereafter, the physician removes his fingers from the mother's vagina, grasps the outer ends of the driving tube and the guide tube, and slides these tubes as a unit off the wires, leaving only the electrodes and the two twisted wires within the mother. The wires are then connected to a fetal monitor (see, for example, U.S. Pat. No. 5,199,432).

Monitoring of fetal heart rate trends through the use of an EKG electrode has long been used to indicate fetal well-being during labor and delivery. By using heart rate trends derived from the fetal EKG signal, the physician is able to infer the adequacy of oxygenation in the fetus. However, this technique is indirect and thus unsatisfactory since it is only after oxygen starvation has occurred for some time that it is reflected in the heart rate record. In addition, the heart rate record itself is subject to errors due to uterine contractions and other artifacts.

To directly monitor blood oxygenation, pulse oximeters are used. Pulse oximeters monitor blood oxygen content by measuring the absorption of light in an arterialized vascular bed. Since oxyhemoglobin and deoxyhemoglobin absorb light differently, the relative concentration of each blood component and thus the percentage oxygen saturation ($SpO_2$) can be determined by measuring absorbed light at two different wavelengths. This method of pulse oximetry is now an established standard of care during anesthesia and in neonatal and adult critical care.

The basic design of any pulse oximeter probe contains red and infra-red light emitting diodes (LEDs) and a photodetector. These components are arranged so that the LEDs illuminate a particular section of arterialized tissue and the detector collects the light from the LEDs which has been transmitted through the tissue section but not absorbed by the skin, bone, blood and other physiologic absorbers. The steady state and time varying components of this signal are then used to calculate the fraction of the arterial blood which is oxygenated.

A vital aspect of a successful design is that the light which is received at the detector must have come only from within the tissue section being illuminated and not directly from the LEDs without having been attenuated in any way by the tissue section.

In pulse oximeter probes intended for use on adults or neonates, this may easily be arranged by utilizing a probe configuration which permits the LED emitters and the detector to be positioned on opposite sides of a section of tissue, for example a finger, toe or ear lobe on an adult or the foot of a neonate.

However, in the case of a presenting fetus where only a small section of the head is accessible, this approach is not viable, and instead reflection pulse oximetry must be employed. In this scheme, the LEDs and photodetector are placed on the same tissue surface and the photodetector receives light which has been scattered from blood vessels within the tissue section. By using reflection pulse oximetry, the potential for errors due to light being transmitted directly from the LEDs to the detector is obviously increased.

Over the years, various devices have been developed which have taken the spiral electrode concept and used the helical spring to attach an additional physiological monitoring device to the scalp, for measuring pH, $PO_2$, or some other metabolic activity.

This approach has potential for fetal reflection oximetry since a miniature optoelectronic hybrid circuit consisting of red and infra-red LEDs and a photodetector could be constructed and placed at the end of the plastic body of the spiral electrode within the coil of the spiral. However, there exist two problems with this concept.

First, in clinical use, a spiral electrode can be attached to the scalp in such a way that a gap exists between the end of the spiral electrode body and the scalp. This has no impact on the efficacy of the spiral as an EKG electrode; however, this gap permits light from the LEDs to travel directly to the photodetector without penetrating the fetal scalp tissue. Thus, oximetry calculations based upon the received signals will not be consistent.

Second, since the LEDs and the photodetector are in close proximity, light must still be prevented from traveling directly between them even when the helical spring has been fully inserted into the fetal scalp and the distal end of the electrode holder is in intimate contact with the skin.

The above problems have been partially addressed by various prior art devices. For example, to eliminate the potential for light directly coupling between the LEDs and the photodetector, prior art devices propose that either the LEDs, or the photodetector, or both be placed below the surface of the fetal skin by means of fiber-optic light guides.

Skin penetration by the fiber-optic light guide ensures that the optical path is confined to perfused tissue. However, these approaches result in at least one additional undesirable puncture in the fetal skin.

It is therefore an object of the present invention to provide a fetal pulse oximetry sensor wherein the sensor is always in intimate contact with the fetal skin, in order to prevent light from travelling directly from the LEDs to the photodetector, with minimal puncturing of the fetal tissue.

It is also an object of the present invention to provide a fetal pulse oximetry sensor wherein the light from the LEDs is prevented from travelling directly to the photodetector when the sensor is in intimate contact with the skin.

It is a further object of the present invention to provide a fetal pulse oximetry sensor that does not cause additional trauma to the fetal skin, viz., punctures.

It is also an object of the present invention to provide a fetal electrode product that includes a fetal heart rate electrode and a pulse oximetry sensor.

SUMMARY OF THE INVENTION

The present invention is for a fetal pulse oximetry sensor device wherein the light emitting portion and light detecting portion of the pulse oximetry sensor are located in the distal portion of the device. In various embodiments of the present invention, one or both of the light emitting portion and light detecting portion are spring biased and moveable in a distal or proximal direction relative to the holder or body of the device. The spring action maintains the pulse oximetry sensor in intimate contact with the fetal tissue. The light emitting portion and the light detecting portion are separated from each other in order to minimize or eliminate the detection of unattenuated light which has not passed through fetal tissue. In accordance with the invention, the fetal pulse oximetry sensor device comprises a coil or spiral extending from the distal surface of the body of the device. Preferably, the coil serves as the fetal electrode of a combined fetal heart rate/pulse oximetry sensor. When the invention comprises only a pulse oximetry sensor, the spiral or coil may be utilized to attach the entire device to the fetus.

In one embodiment of the present invention, the light emitting portion and the light detecting portion are located on the distal surface of a spring biased piston. The spring action maintains the pulse oximetry sensor in intimate contact with the fetal tissue.

In an alternative embodiment, only the light detecting portion is located on the distal surface of the piston, while the light emitting portion is located on the side of the piston, resulting in increased separation between the light emitting portion and the light detecting portion.

Another alternative embodiment has the light detecting portion on the distal surface of the piston, while the light emitting portion is located on an arm extending out from the piston.

In yet another alternative embodiment, the light emitting portion is mounted within the distal end of the body of the device and the light detecting portion is mourned on the opposite side of the distal end of the body. In this embodiment, the body of the device which contains the light emitting portion and the light detecting portion is spring biased in a distal direction relative to the holder in order to maintain intimate contact between the fetal tissue and the light emitting portion and light detecting portion.

BRIEF DESCRIPTION OF THE DRAWINGS

The foregoing brief description or further objects, features and advantages of the present invention will be understood more completely from the following description of presently preferred embodiments with reference to the drawings in which.

DETAILED DESCRIPTION OF THE INVENTION

Figure 1:
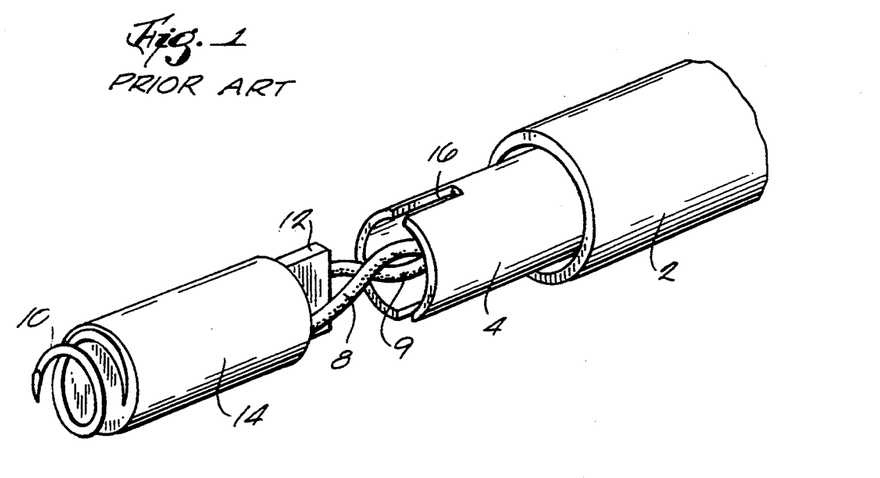
FIG. 1 is a perspective view of a prior an fetal heart rate monitor electrode product.
Figure 2:
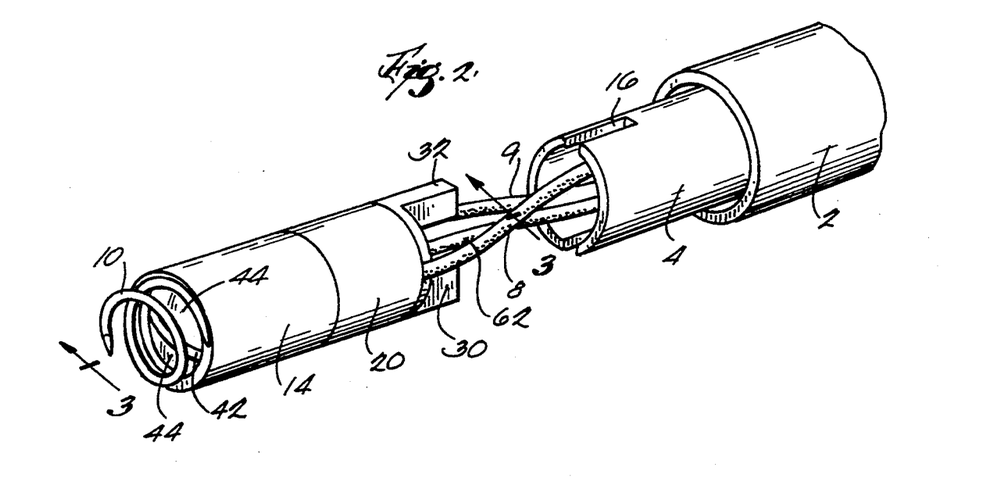
FIG. 2 is a perspective view of a preferred embodiment of a fetal pulse oximetry sensor device containing a pulse oximetry sensor and a fetal heart rate electrode according to the present invention.

FIG. 1 shows the forward end of the conventional fetal electrode product as disclosed in U.S. Pat. No. Re 28,990. The fetal electrode product includes a guide tube 2, driving tube 4 which is of a smaller diameter than that of the guide tube 2, and a twisted pair of wires 8 and 9, the ends of which are connected to respective fetal and reference electrodes 10 and 12. A nonconductive holder 14 electrically insulates the fetal and reference electrodes 10 and 12 from each other. The fetal electrode 10 is in the form of a spiral spring having a pointed end which is driven into the fetal epidermis. The reference electrode 12 is in the form of a plate which is engaged by slots 16 at the forward end of the driving tube 4 to enable the pointed end of the fetal electrode 10 to rotate and be driven into the fetal epidermis by rotation of the driving tube 4.

FIGS. 2-6 illustrate a fetal electrode product modified to include a pulse oximetry sensor in accordance with the preferred embodiment of the invention. In FIGS. 2-6 the numerals of FIG. 1 are used to identify parts that are identical to those shown in FIG. 1.

Figure 3:
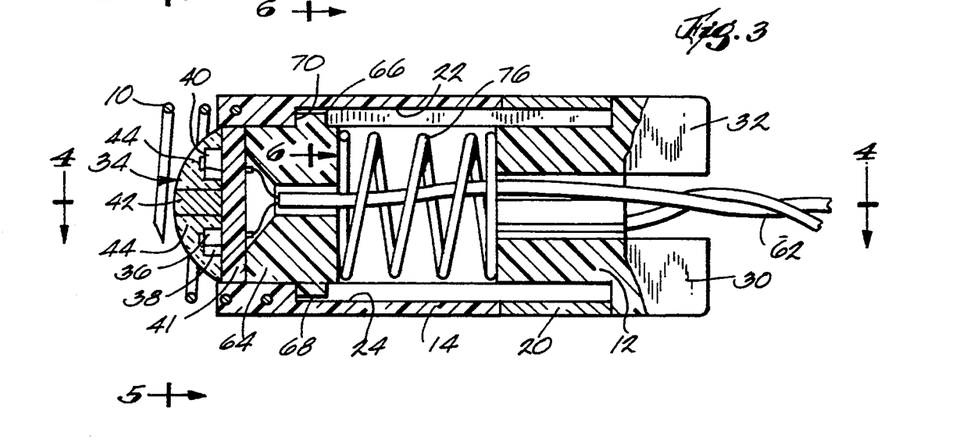
FIG. 3 is a cross section view taken along the line 3—3 of the fetal pulse oximetry device of FIG. 2 showing no insertion of the spiral fetal heart rate electrode.
Figure 4:
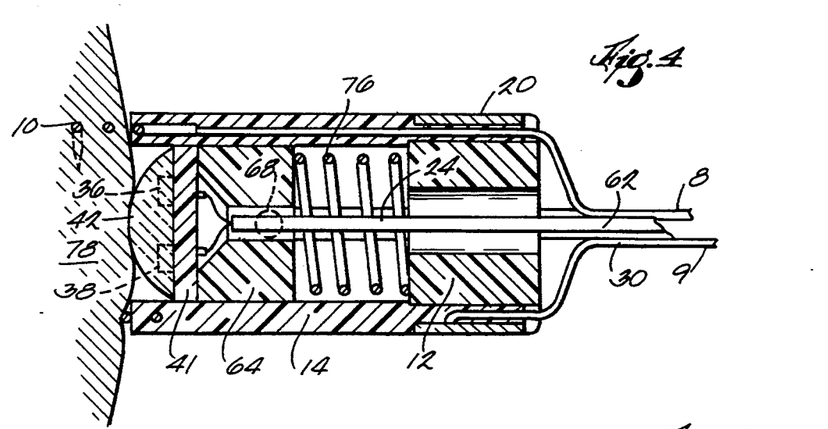
FIG. 4 is a cross section view taken along the line 4—4 of the fetal pulse oximetry sensor device of FIG. 3 showing full insertion of the spiral fetal heart rate electrode.

In accordance with the invention, the insulated holder for the electrodes comprises a cylinder 14 with the fetal spiral electrode 10 being embedded in the distal portion of the holder as shown in FIGS. 3 and 4. The holder 14 is made of insulating material in order to electrically isolate the fetal electrode 10 from the reference electrode 20; however, when the device of the present invention does not include a fetal heart rate monitor, the holder 14 need not be constructed entirely from nonconductive material since it does not have to electrically isolate the fetal electrode 10 and reference electrode 20. The reference electrode comprises an annular ring 20 secured in a notch (not numbered) in the proximal end of the cylindrical holder 14 as shown in FIG. 4. The cylindrical holder 14 includes diametrically opposed slots 22 and 24 which, as shown in FIG. 3, extend from a point just proximal of the embedded end of coil 10 to the proximal surface of the holder 14. Drive nut 12 attached to holder 14 retains the reference electrode 20 onto the holder 14 and includes fins 30 and 32 which are similar mechanically to the plate electrode 20 (FIG. 1) in that they engage the slots 16 of driving tube 4 to enable the electrode to be rotated.

As shown in FIG. 4, the electrodes 10 and 20 are connected to the wires 8 and 9 to couple the fetal EKG signals back to the monitoring equipment.

Figure 5:
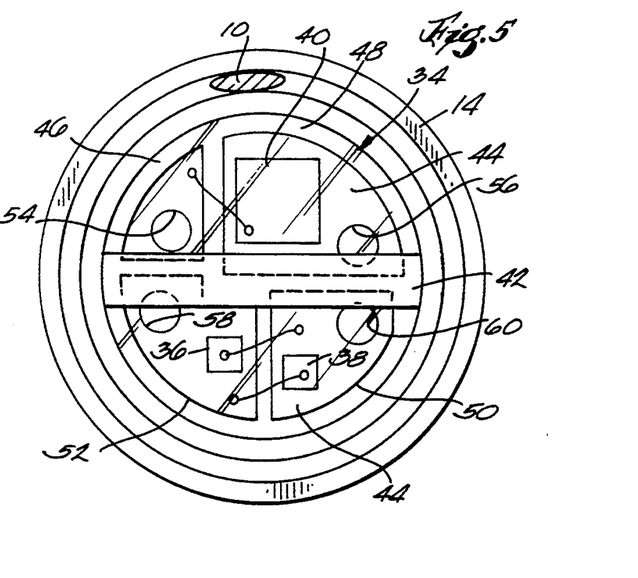
FIG. 5 is a cross section view taken along the line 6—6 of FIG. 3 and showing the front end of the pulse oximetry sensor device containing the hybrid optoelectronic circuit and light blocker.
Figure 6:
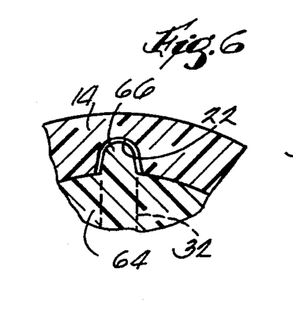
FIG. 6 is a sectional view taken along line 6—6 of FIG. 3 and showing a key arrangement that maintains the reference electrode and holder portion in relative position when the fetal pulse oximetry sensor device is rotated.

FIGS. 3 and 4 show the forward portion of the electrode product containing the pulse oximetry sensor 34. The pulse oximetry sensor 34 is in the form of an optoelectronic hybrid circuit, as is shown in FIG. 5. The hybrid circuit includes a red LED 36 and an infrared LED 38, as well as a photodiode or photodetector 40. These elements are supported on a substrate circuit board 41. The hybrid circuit is constructed such that a light blocker 42 is placed between the LEDs 36, 38 and the photodiode 40 to prevent light from the LEDs from directly impinging on the photodiode 40. The light blocker is constructed from any material which is opaque to both visible and infrared light, e.g. metal. Clear epoxy 44 is then placed over the LEDs 36, 38 and photodetector 40 in order to protect these components and their associated wiring. The clear epoxy 44 should not extend upward over the light blocker 42. Otherwise, the clear epoxy 44 will couple light directly from the LEDs 36, 38 over the light blocker 42 and onto the photodetector 40.

The hybrid circuit 34 contains conductive traces 46, 48, 50, and 52 on the distal face of substrate 41. Conductive traces 46 and 48 provide electrical contact from pins 54 and 56 to photodetector 40. Similarly, conductive traces 50 and 52 provide electrical contact from pins 58 and 60 to LEDs 36 and 38. Pins 54, 56, 58, and 60 extend through board 41 and are connected to individual conductors 53, 55, 57 and 59 of cable 62 which exits the electrode body. Conductors 53, 55 are for photodetector 40, while conductors 57, 59 are for LEDs 36, 38. Alternatively, the pins 54, 56, 58, and 60 may be replaced by plated through holes in board 41 connecting to solder pads on the underside of the board 41, to which the individual conductors 53, 55, 57, and 59 of cable 62 are attached.

In general, the pulse oximetry sensor used in the preferred embodiment of the invention is conventional. Light from the LEDs 36 and 38 is directed into the fetal epidermis and reflected back to the photodiode 40. The light transmitted by the LEDs is attenuated by the fetal tissue and then received by the photodiode 40. Processing circuitry associated with the pulse oximetry sensor determines the oxygen saturation of the blood based on the attenuation of the red and infrared light beams. The light beams received by the photodetector 40 each have a pulsatile and nonpulsatile component. The nonpulsatile components are due to the attenuation of time invariant physiologic blockers such as skin and bone. This is referred to as the DC component. The pulsatile component, on the other hand, represents the attenuation of light during arterial blood flow. This signal is time varying and is often referred to as the AC component. Additionally, the pulsatile components are different for red and infrared light. This difference is due to the fact that hemoglobin and oxyhemoglobin have different optical characteristics. Both hemoglobin and oxyhemoglobin behave similarly with respect to infrared light; however, for red light, the absorption coefficient for hemoglobin is quite different than that of oxyhemoglobin. Thus, the difference in the pulsatile components can be used to derive the level of oxyhemoglobin, and the oxygen saturation of the blood can be computed based on the Lambert-Beers law.

In the ideal situation, the sensor 34 abuts against the fetal scalp 78 as shown in FIG. 4, in which case the light blocker 42 prevents light from the LEDs 36, 38 from passing directly (i.e., without passing through the fetal epidermis) to the photo detector 40. In practice, however, the extent to which the fetal coil 10 penetrates the fetal epidermis 78 is not constant; therefore, the possibility exists that the oximetry sensor 34 will not touch the fetal epidermis 78 which, as explained above, can give rise to errors in the oximetry measurements. In accordance with the invention, the likelihood of such errors is substantially reduced, if not altogether eliminated, by virtue of the fact that the pulse oximetry sensor 34 is spring biased so that regardless of the extent of penetration of coil 10, the distal face of the oximetry sensor 34 will be urged into contact with the fetal epidermis 78, ensuring that light from the LEDs 36 and 38 will pass through the fetal epidermis before reaching the photo detector 40.

In accordance with the preferred embodiment of the invention, the pulse oximetry sensor hybrid circuit 34 is constructed on a board 41 and the board 41 is mounted on the distal face of a piston 64 which fits within a bore through the center of the nonconductive cylindrical holder 14. The substrate circuit board 41 may be any shape as long as it can be mounted on the distal face of the piston 64 and may be attached to the piston 64 by an adhesive. Alternatively, the hybrid circuit substrate 41 can be formed as an integral portion of the piston 64. Piston 64 includes ears 66 and 68 which slide within the slots 22 and 24 to prevent rotation of the piston relative to the cylindrical holder while permitting relative axial movement. The piston 64 is biased in a distal direction by a spring 76. The spring 76 is positioned between the proximal face of the piston 64 and the distal end of the drive nut 12. Since the drive nut 12 is fixedly attached to the holder 14, the spring 76 can only act in the distal direction and urge the piston 64 in a distal direction. The forward or distal movement of piston 64 is limited by the abutment of ears 66 and 68 against shoulders 70 and 72, respectively, which are formed at the distal ends of slots 22 and 24.

The board 41, piston 64, and spring 76 are inserted in the holder 14 via the proximal end of the holder 14. The drive nut 12 is then positioned in the proximal end of the cylindrical holder 14 in order to restrain the piston 64, spring 76, and reference electrode 20, as shown in FIGS. 3 and 4. The arrangement of piston ears 66 and 68 within slots 22 and 24 maintains the piston 64 (and the hybrid circuit 34 which is mounted on the piston 64) and the holder 14 in the same relative radial position when the entire electrode product is rotated.

Alternative biasing means such as soft rubber, a fluid filled balloon, or other biasing means may be employed in place of spring 76. Additionally, while the spiral fetal electrode 10 is used to attach the invention to the fetal scalp, alternative attachment means such as adhesives or suction-type devices may also be employed.

FIG. 3 shows the electrode product when the spiral electrode 10 is not inserted into the fetal skin 78. In this instance, the piston 64 is biased by the spring 76 but restrained by the shoulders 70 and 72. Also, the pulse oximetry sensor 34 is pushed distally out of the holder 14. FIG. 4 shows the electrode product in use, with the spiral electrode 10 being rotatably engaged in the fetal skin 78. As the spiral electrode 10 is rotated into the fetal skin 78, the fetal skin 78 pushes the pulse oximetry sensor 34 and the piston 64 proximally into the holder 14. However, at the same time, the spring 76 is acting to push the piston 64 and the pulse oximetry sensor 34 distally out of the holder 14. In this manner, the action of the inward force exerted by the fetal skin 78 and the outward force exerted by the spring 76 operate to maintain the hybrid circuit 34 in intimate contact with the fetal skin 78. Thus, the light from the LEDs 36, 38 is prevented from travelling directly from the LEDs 36, 38 to the photodiode 40. Also, this result is achieved without causing additional trauma to the fetal skin.

Figure 7:
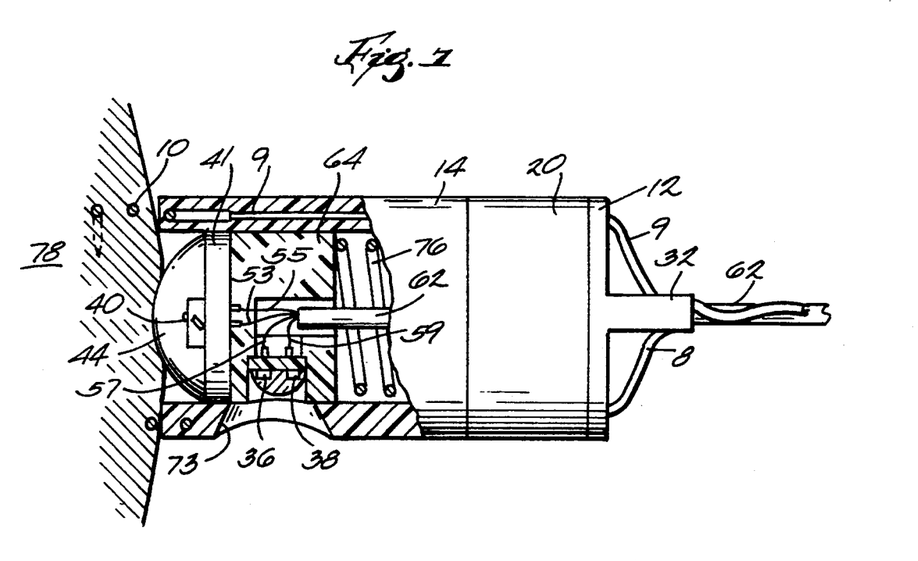
FIG. 7 is a cross section view similar to FIG. 4, but of an alternative fetal pulse oximetry sensor device containing the hybrid optoelectronic circuits with the LEDs radially mounted on the side.

In an alternative embodiment (shown in FIG. 7), only the photodiode 40 is mounted on the distal surface of piston 64. The LEDs 36 and 38 are instead mounted in a side of the piston 64, at a point slightly proximal of the distal surface of piston 64. In this embodiment, the red and infrared beams of LEDs 36 and 38 shine radially outwardly through an opening 73 in the holder 14. The opening 73 does not extend all the way to either the distal surface or the proximal surface of the holder 14, such that at the distal surface, the holder 14 is still interposed between the photodiode 40 and the LEDs 36 and 38. This arrangement provides for better optical separation between the photodiode 40 and the LEDs 36 and 38, and therefore, the amount of unattenuated light travelling directly from the LEDs 36 and 38 to the photodiode 40 is significantly reduced. Additionally, in this embodiment there is no need for the light blocker 42, since the piston 64 and the holder 14 act to isolate the LEDs 36 and 38 from the photodiode 40.

Figure 8:
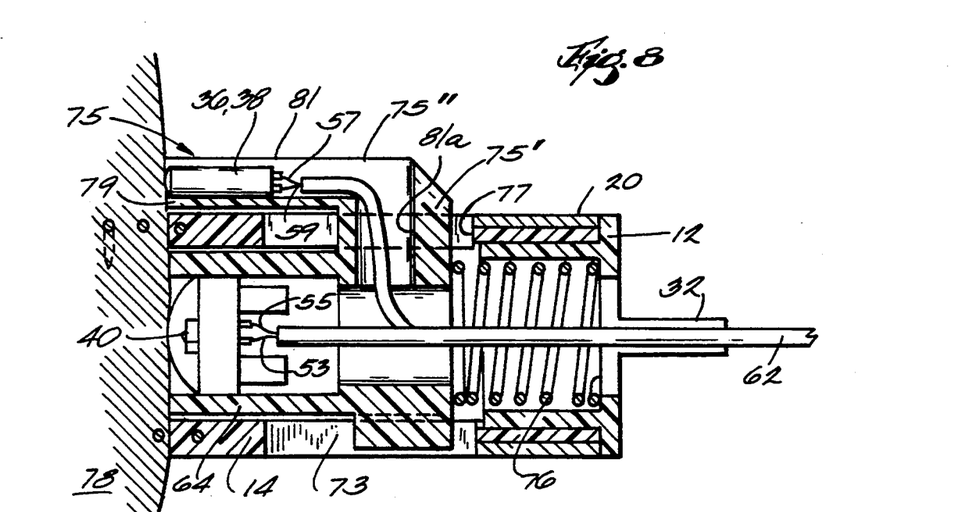
FIG. 8 is a cross section view similar to FIG. 4, but of an alternative front end of the fetal pulse oximetry sensor device containing the hybrid optoelectronic circuits with the LEDs mounted on an arm extending out the side of the cylindrical holder.

In yet another alternative embodiment (shown in FIG. 8), only the photodiode 40 is mounted on the distal surface of piston 64, while the LEDs 36 and 38 are mounted on the distal face of an L-shaped external arm 75 which is part of the proximal end of piston 64. The short portion 75' of the arm 75 is part of the proximal end of piston 64 and extends radially through a slot 77 formed in the holder 14. A long portion 75" of the L-shaped arm 75 extends at a right angle to the short portion 75' at a point external to the holder. The long portion 75" extends axially in a distal direction to a point even with the distal surface of holder 14. The LEDs 36, 38 are mounted on the distal face of the long member 75" of arm 75.

During operation, the spring 76 urges the piston 64 and the attached arm 75 in the distal direction. In this way, the photodiode 40 mounted on the distal surface of the piston 64 and the LEDs 36 and 38 mounted on the distal face of the arm 75 are maintained in intimate contact with the fetal skin 78. The slot 77 through which the arm 75 travels, does not extend all the way to the distal end of the holder 14, in order to have the holder 14 still interposed between the photodetector 40 and the LEDs 36, 38. Also interposed between the photodetector 40 and the LEDs 36, 38 is the inside wall 79 of the long member 75". This arrangement provides even more optical separation between the photodiode 40 and the LEDs 36 and 38, due to the increased distance between the photodiode 40 and the LEDs 36 and 38. In addition, in this embodiment, the light blocker 42 (FIGS. 2-5) is no longer needed since the holder 14 and the extending arm 75 act to isolate the LEDs 36 and 38 from the photodiode 40. A slot 81 in the long portion 75" communicates with a transverse bore 81a to allow for the insertion of LEDs 36, 38. Electrical contact to LEDs 36, 38 is provided by two conductor 57, 59 of cable 62 that are connected to LEDs 36, 38 and extend through long member 75" into short member 75' of arm 75 and into the holder 14. Similarly, photodetector 40 is connected by two conductors (53, 55) of cable 62. Cable 62 travels through the holder 14, exits the proximal end of holder 14, and continues to external monitoring equipment (not shown). Cables 8 and 9 (not shown) are also connected to the monitoring equipment.

In yet another alternative embodiment (shown in FIGS. 9-11), the device is constructed with a cylindrical outer housing 114 inside of which is a holder 164. In this embodiment, the LEDs 36, 38 and photodetector 40 are mounted at the distal end of housing 114. The photodetector 40 and LEDs 36, 38 are each mounted within respective recesses 98 and 100 formed at the distal face of the housing 114. The recesses 98, 100 may be of variable depth, as long as the optical components, LEDs 36, 38 and photodetector 40, are positioned such that they do not extend beyond the distal surface of housing 114. This is to prevent any light from travelling directly from the LEDs 36, 38 to the photodetector 40 without having first been attenuated by the fetal skin 78. Preferably, the LEDs 36, 38 and the photodetector are mounted diametrically opposite each other at the distal surface of housing 114, in order to increase the separation distance between the LEDs 36, 38 and the photodetector 40. However, the LEDs 36, 38 and photodetector 40 may be mounted in other relative positions, as long as the LEDs 36, 38 are isolated from photodetector 40. The LEDs 36, 38 are supported by a substrate circuit board 80 mounted within recess 100. Similarly, photodetector 40 is supported by substrate circuit board 82 mounted within recess 98.

Figure 9:
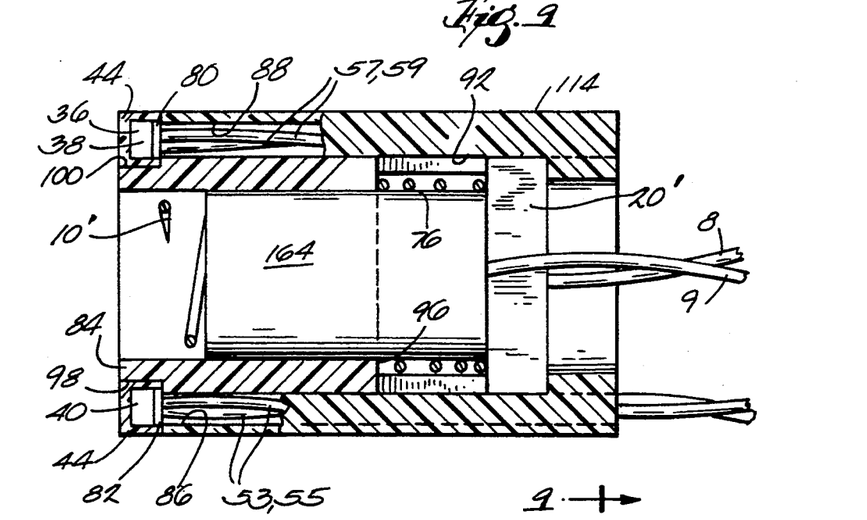
FIG. 9 is a sectional view of the fetal pulse oximetry device where the LEDs and photodetector are mounted within the sidewalls of the holder portion.

An opaque or light blocking cylindrical tube 84 is positioned within the housing 114 at its distal end. The tube 84 acts to isolate the photodetector 40 from the LEDs 36, 38 and prevent light from travelling directly from the LEDs 36, 38 to the photodetector 40 without having first been attenuated by the fetal skin 78. Tube 84 is shorter in length than housing 114 and thus forms a shoulder 96 for restraining bias spring 76. Recesses 98, 100 are then filled with clear epoxy 44, in order to protect the optical components, LEDs 36, 38 and photodetector 40, contained therein.

The conductors 53, 55 for photodiode 40 travel through an axial conduit 86 within the housing 114, which extends from the recess 98 to the proximal end of the housing 114. Similarly, conductors 57, 59 for LEDs 36, 38 travel through an axial conduit 88 within the housing 114, which extends from the recess 100 to the proximal end of housing 114.

As is illustrated in FIG. 9, in this embodiment, the spiral fetal electrode or fetal attachment means 10' is mounted on the distal face of holder 164, and both the attachment means 10' and the holder 164 are received within the housing 114. Also, the attachment means 10' of the invention of FIG. 9 has a smaller diameter than the attachment means 10 of FIGS. 2-5. This is because in FIGS. 2-5, the attachment means 10 is attached to the distal end of the holder 14 and is therefore substantially equal in diameter to the diameter of holder 14. However, in the embodiment shown in FIG. 9, attachment means 10′ is mounted on the distal end of holder 164 which fits within a bore formed within housing 114. Therefore, the diameter of attachment means 10′ is smaller than the diameter of housing 114, which is substantially equal to the diameter of holder 14 in FIGS. 2–5.

As is shown in FIG. 9, the diameter of the bore formed within housing 114 is smaller at the distal end in comparison with the bore diameter at the proximal end. The reduced diameter of the bore at the distal end is due to the presence of tube 84. This reduced diameter corresponds to the diameter of holder 164 and attachment means 10′. The larger diameter bore at the proximal end of housing 114 allows additional space for spring 76 which is positioned around holder 164.

Attached to the proximal end of holder 164 is a rectangular shaped rear portion 20′. In the case where the device of the present invention includes a fetal heart monitor, rear portion 20′ may be used as the reference electrode. Reference electrode 20′ is wider than holder 164. Positioned distal to the reference electrode 20′ and around the holder 164 is the spring 76. The spring 76 is restrained at its proximal end by reference electrode 20′ and at its distal end by shoulder 96 formed by the proximal end of tube 84. In this embodiment, attachment means 10′ is attached to the fetal skin, and since attachment means 10′ is also fixedly attached to holder 164 and reference electrode 20′, spring 76 acts on shoulder 96 to urge the housing 114 in a distal direction with respect to the holder 164. In this way, the photodetector 40 and LEDs 36, 38 which are mounted at the distal end of housing 114 are maintained in intimate contact with the fetal skin.

Alternatively, the rear portion of the holder 164 may incorporate a pair of radially extending ears (not shown) on opposite sides of the proximal end of holder 164 which restrain the proximal end of spring 76.

The configuration of this embodiment of the present invention eliminates the need for a separate light blocker since any unattenuated light which would travel directly from the LEDs 36 and 38 to the photodiode 40 is prevented from reaching the photodiode 40 by tube 84. Also, this configuration provides for improved optical separation between the LEDs 36, 38 and the photodiode 40, since the tube 84 provides a physical barrier between the LEDs 36, 38 and the photodiode 40. In addition, the optical separation is improved due to the fact that the photodiode 40 is further away from the LEDs 36 and 38.

Figures 10, 11:
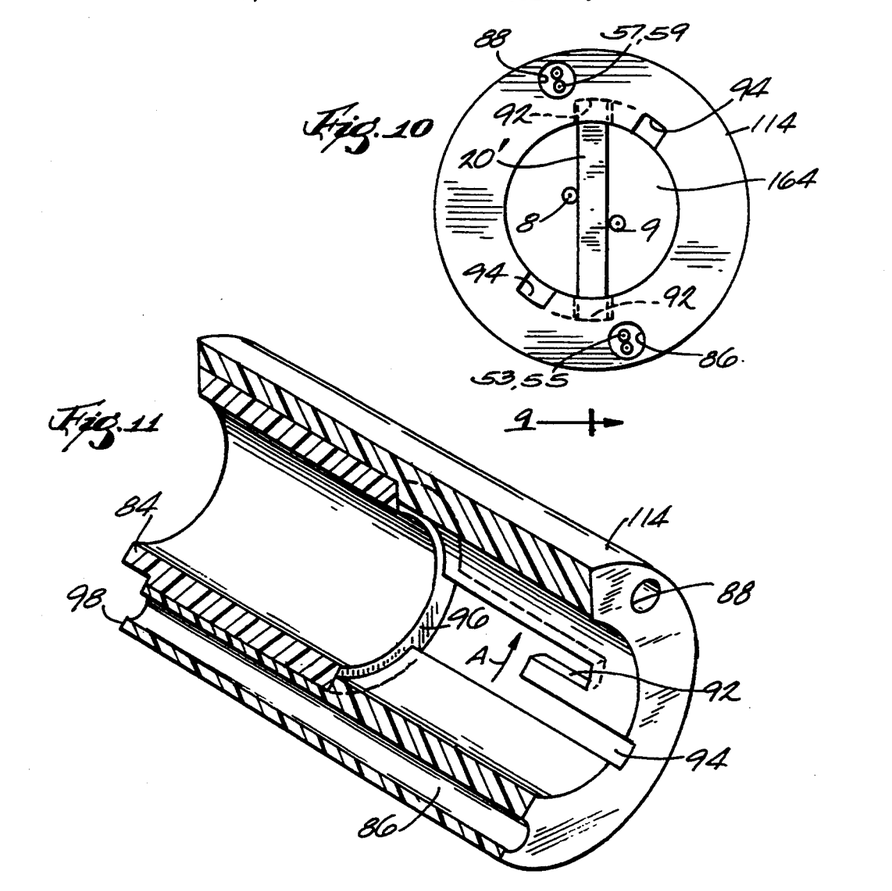
FIG. 10 is an end view of the fetal pulse oximetry device of FIG. 9.
FIG. 11 is a sectional perspective view of the fetal pulse oximetry sensor device of FIG. 9 showing the latch mechanism for inserting the spring and piston assembly.

Referring now to FIG. 11, attachment means 10′, holder 164, spring 76, and reference electrode 20′ are inserted into the housing 114 at the proximal end of housing 114. During insertion, attachment means 10′, holder 164, and spring 76 are inserted into the bore at the proximal end of the housing 114; however, since the reference electrode 20′ is larger than the holder 164, it is received within a recessed insertion channel 94 formed in the inside surface of the proximal portion of housing 114. The insertion channel 94 extends from the proximal end of housing 114 to the proximal end of tube 84 where the shoulder 96 is formed. The reference electrode 20′ is then pushed distally and twisted in the direction of arrow A in order to be received within inner channel 92. As shown in FIG. 11, inner channel 92 does not extend all the way to the proximal end of housing 114, and thus limits the proximal travel of reference electrode 20′ and the attached holder 164. The inner channel 92 which receives the reference electrode 20′ is in the form of a longitudinal slot, such that when the device is rotated, there is no relative radial movement between the housing 114 and the reference electrode 20′ and the attached holder 164. The herein described assembly for insertion of the attachment means 10′, holder 164, and reference electode 20′ is commonly referred to as a "bayonet lock". Other similar assemblies for insertion and locking may be employed.

While the housing 114 and tube 84 are shown in FIGS. 9 and 10 as generally cylindrical members, it is to be understood that the housing 114 and tube 84 received therein may be formed in a variety of shapes such as oval or elliptical, without affecting the operation of the present invention.

During operation, the spiral electrode or attachment means 10′ is embedded in the fetal epidermis 78. Since the holder 164 and reference electrode 20′ are attached to the spiral electrode 10′, spring 76, which is positioned between reference electrode 20′ and shoulder 96, urges housing 114 in a distal direction relative to holder 164, causing the embedded photodiode 40 and LEDs 36 and 38 to be maintained in intimate contact with the fetal epidermis 78.

The present invention in this preferred embodiment is intended for use with the basic electrode of U.S. Pat. No. Re 28,990, as shown in FIG. 1. It is also possible to use the invention as a pulse oximetry sensor alone, for example with the coil being used solely to secure the sensor device to the fetal epidermis.

While the foregoing description and drawings represent the preferred embodiments of the present invention, it will be understood that various changes and modifications may be made without departing from the spirit and scope of the present invention.

What is claimed is:

1. A fetal pulse oximetry device, comprising:
   a holder having distal and proximal ends;
   attaching means on said holder for attaching said device to a fetus;
   a pulse oximetry sensor including light emitting means and light detecting means; and
   means supporting at least one of said light emitting means and light detecting means for distal and proximal movement relative to said holder.

2. A fetal pulse oximetry device according to claim 1, further comprising means for biasing the supporting means distally with respect to said holder.

3. A fetal pulse oximetry device according to claim 2, further comprising means for preventing rotation of said supporting means with respect to said holder and stop means for limiting the distal movement of said supporting means.

4. A fetal electrode product comprising:
   a holder having distal and proximal ends;
   attaching means on said holder for attaching said electrode product to a fetus;
   a piston mounted within a bore in the distal end of the holder, the piston having a distal end and a proximal end, the distal end being adjacent to the attaching means;
   a pulse oximetry sensor including light emitting means and light detecting means, wherein at least one of said light emitting means and light detecting means is mounted on the piston; and means supporting said piston for distal and proximal movement relative to said holder.

5. A fetal electrode product according to claim 4, wherein the support means comprises spring means to bias the piston toward the distal end of the holder to maintain the pulse oximetry sensor in intimate contact with fetal tissue.

6. A fetal electrode product according to claim 5, wherein the light emitting means sensor comprises:
a red LED which emits red light into the fetal tissue;
an infrared LED which emits infrared light into the fetal tissue; and
said light detecting means comprising a photodetector which detects the red light and the infrared light which has passed through the fetal tissue.

7. A fetal electrode product according to claim 6, wherein the pulse oximetry sensor further comprises a light blocker positioned between the photodetector and the red and infrared LEDs, the light blocker being of a material opaque to red light and infrared light.

8. A fetal electrode product according to claim 7, wherein the light blocker comprises a metallic material.

9. A fetal electrode product according to claim 7, wherein the pulse oximetry sensor further comprises a light transparent material placed over the red and infrared LEDs and the photodetector, the light transparent material having a height less than a height of the light blocker.

10. A fetal electrode product according to claim 9, wherein the light transparent material comprises a clear epoxy resin.

11. A fetal electrode product according to claim 6, further comprising electrical leads connected to said LEDs and photodetector, said electrical leads passing through said piston, spring and annular seat.

12. A fetal electrode product according to claim 6 wherein the photodetector is mounted on the distal end of the piston, and the red LED and infrared LED are mounted in a side of the piston and wherein an opening is provided in the holder, such that the red light and infrared light are emitted by said LEDs through said opening.

13. A fetal electrode product according to claim 6 wherein the photodetector is mounted on the distal end of the piston, and the red LED and infrared LED are mounted on an arm, the arm being external to the holder and attached to the piston.

14. A fetal electrode product according to claim 5, further comprising an annular seat fixed adjacent the proximal end of said holder, said piston having a proximal surface and said annular seat having a distal surface, said spring means being situated between the proximal surface of said piston and a distal surface of said annular seat.

15. A fetal electrode product according to claim 4, further comprising a fetal heart rate electrode, the fetal heart rate electrode comprising a spiral fetal electrode attached to the distal end of the holder and a reference electrode attached to the proximal end of the holder, the spiral fetal electrode and the reference electrode being electrically isolated from each other.

16. A fetal electrode product according to claim 15, wherein said reference electrode comprises a ring mounted on the proximal end of said holder.

17. A fetal pulse oximetry device comprising:
a holder having attaching means for attaching said device to a fetus;
a housing movably mounted relative to said holder and having distal and proximal ends;
a pulse oximetry sensor including light emitting means and light detecting means mounted at the distal end of said housing;
light blocking means positioned between the light emitting means and the light detecting means; and
means for biasing the housing for movement in a distal direction with respect to the holder.

18. A fetal pulse oximetry device according to claim 17, wherein the biasing means comprises a spring.

19. A fetal pulse oximetry device according to claim 17, wherein the light emitting means of the pulse oximetry sensor comprises a red LED which emits red light into the fetus and an infrared LED which emits infrared light into the fetus, and the light detecting means comprises a photodetector which detects the red light and the infrared light passing through the fetus.

20. A fetal pulse oximetry device according to claim 17, wherein the pulse oximetry sensor further comprises light transparent material placed over the light emitting means and the light detecting means.

21. A fetal pulse oximetry device according to claim 20, wherein the light transparent material comprises a clear epoxy resin.

22. A fetal pulse oximetry device comprising:
a holder having attaching means for attaching said device to a fetus;
a housing having distal and proximal ends;
a pulse oximetry sensor including light emitting means and light detecting means mounted at the distal end of said housing;
light blocking means positioned between the light emitting means and the light detecting means; and
a spring for biasing the housing in a distal direction with respect to the holder,
said holder being positioned within a bore in the housing and having a proximal end, the proximal end of the holder being connected to a rear portion which is larger than the holder, and the spring being positioned externally around the proximal end of holder and restrained by the rear portion, such that the spring acts on a shoulder formed within the bore of the housing to bias the housing in the distal direction with respect to the holder.

23. A fetal pulse oximetry device according to claim 22 further comprising a fetal heart rate electrode having a fetal electrode and a reference electrode, wherein the attaching means comprises the fetal electrode and the rear portion comprises the reference electrode.

* * * * *